(12) United States Patent
Janas et al.

(10) Patent No.: US 11,254,903 B2
(45) Date of Patent: Feb. 22, 2022

(54) METHOD AND SYSTEM FOR SUSPENSION CULTURE

(71) Applicant: Cytiva Sweden AB, Uppsala (SE)

(72) Inventors: Michelle Louise Janas, Cardiff (GB); Aaron Dulgar Tulloch, Niskayuna, NY (US); Clive Glover, Cardiff (GB)

(73) Assignee: CYTIVA SWEDEN AB, Uppsala (SE)

( * ) Notice: Subject to any disclaimer, the term of this patent is extended or adjusted under 35 U.S.C. 154(b) by 106 days.

(21) Appl. No.: 15/328,763

(22) PCT Filed: Jul. 9, 2015

(86) PCT No.: PCT/EP2015/065683
§ 371 (c)(1),
(2) Date: Jan. 24, 2017

(87) PCT Pub. No.: WO2016/012249
PCT Pub. Date: Jan. 28, 2016

(65) Prior Publication Data
US 2017/0211027 A1    Jul. 27, 2017

Related U.S. Application Data

(60) Provisional application No. 62/028,877, filed on Jul. 25, 2014.

(30) Foreign Application Priority Data

Sep. 16, 2014  (GB) ...................................... 1416362

(51) Int. Cl.
*C12M 1/00*         (2006.01)
*C12M 3/06*         (2006.01)
(Continued)

(52) U.S. Cl.
CPC ............ *C12M 23/14* (2013.01); *C12M 23/26* (2013.01); *C12M 27/16* (2013.01); *C12M 29/10* (2013.01);
(Continued)

(58) Field of Classification Search
CPC ..... C12N 5/0636; C12M 41/48; C12M 29/10; C12M 41/34; C12M 41/36; C12M 23/26; C12M 23/14; C12M 27/16; C12M 41/32
See application file for complete search history.

(56) References Cited

U.S. PATENT DOCUMENTS 6,190,913 B1   2/2001   Singh
6,284,453 B1   9/2001   Siano
(Continued)

FOREIGN PATENT DOCUMENTS

CN   1238498   *   1/2006   ............... C12N 5/16
JP   S52125686 A      10/1977
(Continued)

OTHER PUBLICATIONS

Kyung et al. (High density culture of mammalian cells with dynamic perfusion based on on-line oxygen uptake rate measurements. Cytotechnology 14:183-190, 1994).*
(Continued)

*Primary Examiner* — Sean C. Barron
(74) *Attorney, Agent, or Firm* — Eversheds Sutherland (US) LLP

(57) ABSTRACT

The present invention relates to cell culture in bioreactors, such as flexible cellbag bioreactors. More closely the invention relates to a method and system for determining the cell density in a bioreactor culture and for controlling the perfusion rate of a suspension culture of cells in a bioreactor, comprising measuring the oxygen uptake of primary mononuclear cells in a non-static bioreactor.

11 Claims, 4 Drawing Sheets

1) computer terminal
2) cellbag control unit
3) Gas line
4) DO optical cable
5) Xuri cell expansion system
6) Rocking platform
7) cellbag bioreactor
8) Gas inlet
9) DO optical sensor
10) media waste line
11) media feed line
12) pump unit
13) media feed reservoir
14) media waste reservoir

(51) Int. Cl.
C12M 1/34 (2006.01)
C12M 1/36 (2006.01)
C12N 5/0783 (2010.01)

(52) U.S. Cl.
CPC ............ C12M 41/32 (2013.01); C12M 41/34 (2013.01); C12M 41/36 (2013.01); C12M 41/48 (2013.01); C12N 5/0636 (2013.01)

(56) References Cited

U.S. PATENT DOCUMENTS

2007/0178586 A1* 8/2007 Yang .................. C12M 23/58 435/325
2012/0329151 A1 12/2012 Baskar et al.
2014/0011270 A1 1/2014 Chotteau et al.

FOREIGN PATENT DOCUMENTS

| JP | H03172172 A | 7/1991 |
| JP | H05123156 A | 5/1993 |
| JP | H0838166 A | 2/1996 |
| WO | 01/23520 A1 | 4/2001 |
| WO | 2011/005773 A2 | 1/2011 |

OTHER PUBLICATIONS

GE Healthcare Life Sciences. Perfusion culture of T lymphocytes in the WAVEW Bioreactor System 2/10.2011, pp. 1-6).*
Ochoa et al. (Oxygen uptake rate in microbial processes: An overview. Biochemical Engineering Journal 2010, 49: 189-307).*
Miller et al. (Effects of Dissolved Oxygen Concentration on Hybridoma Grown and Metabolism in Continuous Culture. Journal of Cellular Physiology 132:524-530 (1987).*
Hanson et al. (Comparisons of Optical pH and Dissolved Oxygen Sensors With Traditional Electrochemical Probes During Mammalian Cell Culture. Biotechnology and Bioengineering, vol. 97, No. 4 (2007).*
Singh et al. (On-Line Measurement of Oxygen Uptake in Cell Culture Using the Dynamic Method. Biotechnology and Bioengineering, vol. 52, pp. 443-448 (1996).*
GE Healthcare (Wave Bioreactor 2/10 and 20/50 systems. pp. 1-6, first published online Feb. 2009).*
GE Healthcare (Xuri Cell Expansion System W25 (GE Healthcare Life Sciences; published Jul. 15, 2013. pp. 1-8).*
Jones et al. (Automatic Tuning PID Controller For Dissolved Oxygen Concentration In Fermentation Processes. pp. 1-268, 1995).*
Study.com. (What is a Trend Line in Math?—Definition, Equation & Analysis. pp. 1-5. 2019).*
Kyung Y-S et al. "High Density Culture of Mammalian Cells with Dynamic Perfusion Based on On-Line Oxygen Uptake Rate Measurements", Cytotechnology, Kluwer Academic Publishers, Dordrecht, NL, vol. 14, Jan. 1, 1994.
Ruffieux et al., "Measurement of volumetric (OUR) and determination of specific (q02) oxygen uptake rates in animal cell cultures", Journal of Biotechnology, vol. 63, No. 2, 1998, pp. 85-95.
Ozturk et al., "Cell Culture Technology for Pharmaceutical and Cell-Based Therapies", published 2005, CRC Press, pp. 405-406.
Blackie et al., "Perfusion rate control based on on-line monitoring of oxygen consumption rates in mammalian cell fermentation", Abstracts of Papers American Chemical Society, 209th American Chemical Society National Meeting, Anaheim, CA, Apr. 2-6, 1995, vol. 209, No. 1-2.
Biotechnology and Bioengineering, vol. 64, No. 3, 1999, Jorjani et al., "Effects of cell density and temperature on oxygen consumption rate for different mammalian cell lines", pp. 349-356.
International Search Report and Written Opinion regarding International Application No. PCT/EP2015/065683, dated Oct. 2, 2015, 9 pages.
GB Search Report regarding GB Application No. 1416362.0, dated Jun. 17, 2015, 5 pages.
Japanese Office Action regarding JP Application No. 2017-502619, dated May 14, 2019, 12 pages.
GE Healthcare Life Sciences, "Perfusion culture of T lymphocytes in the WAVE Bioreactor System 2/10 (software version 2.61)", Application Note 28-9650-52 AC, published Nov. 2011, 6 pages.
Chinese Office Action regarding CN Application No. 201580041144.4, dated Jun. 26, 2019, 12 pages.
Feng et al., "On-line Monitoring of Oxygen Uptake Rate and its Application in Hybridoma Culture", Chinese Journal of Biotechnology, vol. 19, No. 5, published Sep. 2003, pp. 593-597, 5 pages

* cited by examiner 1) computer terminal
2) cellbag control unit
3) Gas line
4) DO optical cable
5) Xuri cell expansion system
6) Rocking platform
7) cellbag bioreactor
8) Gas inlet
9) DO optical sensor
10) media waste line
11) media feed line
12) pump unit
13) media feed reservoir
14) media waste reservoir 15) fastening rod
16) feed in port
17) waste out port
18) gas exhaust tube
19) gas inlet tube
20) perfusion filter (inside cellbag)
21) position of DO sensor (underside of cellbag)
22) harvest port
23) sampling port

METHOD AND SYSTEM FOR SUSPENSION CULTURE

CROSS-REFERENCE TO RELATED APPLICATIONS

This application is a filing under 35 U.S.C. 371 of international application number PCT/EP2015/065683, filed Jul. 9, 2015, which claims priority to U.S. application No. 62/028,877, filed Jul. 25, 2014 and which claims priority to GB application number 1416362.0, filed Sep. 16, 2014, the entire disclosures of each of which are hereby incorporated by reference.

FIELD OF THE INVENTION

The present invention relates to cell culture in bioreactors, such as flexible cellbag bioreactors. More closely the invention relates to a method and system for determining the cell density in a bioreactor culture and for controlling the perfusion rate of a suspension culture of cells in a bioreactor, comprising measuring the oxygen uptake of primary mononuclear cells in a non-static bioreactor,

BACKGROUND OF THE INVENTION

Flexible cell culture bags, are currently used to culture and expand primary peripheral blood mononuclear cells (particularly T cells) for transplantation into patients. Cells are grown within a contained cellbag and high cell densities are achieved by using media perfusion, where fresh media is added to the culture and spent media is removed. The rate of media perfusion is dependent upon the concentration of cells within the cellbag, the perfusion rate increasing with increased cell concentration. Monitoring of the growth rate and concentration of the cultured cells requires sampling from the cellbag. When opened, the sampling port exposes the culture to the external environment which carries the risk of contamination of the culture.

There are a variety of inline (in situ) cell counters that have been developed for monitoring of cell growth of cells grown in suspension cultures. These include optical probes (for example focused beam reflectance measurement (FBRM) probes and particle vision measurement (PVM) system), and in situ microscopes. However these all require probe immersion into the culture from an external source, which compromises sterility. These solutions are also large, expensive and would be difficult to integrate into a cellbag. They are designed to be used with stainless steel bioreactors rather than flexible cellbags.

Optical probes which measure the pH and level of dissolved oxygen (DO) in a bioreactor culture are available. Dissolved oxygen readings can be used to determine the oxygen uptake rate (OUR) of the bioreactor culture. It is understood that that oxygen uptake rates correlate with cell concentration, such as described in for example Eur. J Appl Microbiol Biotechnol (1981) 12:193-197 which shows that the greater the number of cells in the culture, the higher the OUR reading. This method relates to culturing of immortalised cell lines for protein production where maintaining a constant high level of dissolved oxygen is a priority. Dissolved oxygen readings are used to determine whether the agitation rate of the bioreactor should be increased or whether oxygen sparging is required to keep the DO levels above a nominal critical level.

A method to monitor cell growth and regulate perfusion rate of sensitive cells that does not compromise the cells or the closed culture environment would be desired.

SUMMARY OF THE INVENTION

The present inventors have found that an inverse linear relationship exists between dissolved oxygen concentrations and cell density for primary cells cultured in suspension culture. As the number of cell increases, the concentration of dissolved oxygen decreases. The relationship allows cell concentration to be predicted based on the dissolved oxygen reading, thereby negating the requirement to use a sampling port. In the present invention readings of oxygen uptake are used to set the media perfusion rate.

Thus, in a first aspect the invention relates to a method for regulating perfusion rate in a suspension culture of cells in a non-static bioreactor, comprising registering the oxygen uptake of primary mononuclear cells in the bioreactor; predicting the cell number of said primary mononuclear cells by a pre-determined correlation of the registered oxygen uptake with the cell number; and controlling the perfusion rate in response to the registered oxygen uptake. The method is applicable to suspension cultures in any type of rocking, stirred or agitated bioreactor. The bioreactor is preferably kept at a constant rocking rate, preferably at least during the registration of the oxygen uptake.

The registered oxygen uptake is dissolved oxygen (DO) uptake or oxygen uptake rate (OUR), which measures the change in dissolved oxygen over time. In a preferred embodiment of the method, the DO uptake is measured.

Preferably the oxygen uptake is measured by a sensor integrated in the bioreactor. The sensor is preferably an optical sensor which is embedded into the bioreactor, such as in the bottom of a cell bag. A cable may be attached from the outside which leads to a controlling computer. Measurements will be taken continuously and recorded. No manipulation of the bioreactor/cellbag is required.

Preferably the rocking rate of the bioreactor is 1-25 rpm, more preferably 10-15 rpm. The method of the invention is especially suitable for suspension culture of T-cells, or other sensitive cells.

In a preferred embodiment the registered oxygen uptake is dissolved oxygen (DO), the rocking rate is 10-15 rpm and the bioreactor is a flexible cell bag.

In a second aspect, the invention relates to a bioreactor system, comprising a computer terminal (1), a bioreactor control unit (2), a gas outlet line (3), a sensor cable (4), a cell expansion system (5), a rocking platform (6), a bioreactor (7), a gas inlet port (8), a sensor (9), such as an optical probe, for measuring oxygen uptake, a media waste line (10), a media feed line (11), and pump unit (12), a media feed reservoir (13) and a media waste reservoir (14), wherein the pump unit, the cell expansion system and bioreactor control unit are connected to the computer terminal (1) which controls the rate that the pump unit operates which controls the rate of media exchange in response to oxygen uptake readings.

The sensor (9) may be an optical probe or an electrochemical probe.

In a preferred embodiment of the bioreactor system the sensor (9) measures dissolved oxygen (DO) or oxygen uptake rate (OUR).

Preferably sensor is an optical probe which measures DO and is embedded in the bottom of a flexible cell bag.

The invention presents the ability to use dissolved oxygen (DO) readings or oxygen uptake rate (OUR) to guide a perfusion strategy. In embodiments of the invention the perfusion may be automated (by writing a software program) based on DO or OUR readings. Using dissolved oxygen readings to set perfusion rates instead of cell count also enables automation of this process and negates the requirement to manually change perfusion settings, which reduces the chance of human error compromising the culture.

DETAILED DESCRIPTION OF THE INVENTION

The invention will now be described more closely in association with the accompanying drawings and some non-limiting Examples.

The invention is a method to predict the density of primary lymphocytes grown in a bioreactor in situ. The invention uses a linear relationship between dissolved oxygen concentration and cell concentration to predict cell densities in the bioreactor culture. The invention allows perfusion rates to be set based on dissolved oxygen concentrations. A program which would allow perfusion rates to be adjusted based on dissolved oxygen readings can be written into the software that runs any selected bioreactor.

The linear relationship between DO/OUR and cell concentration has never been shown for primary mononuclear cells before. The relationship was surprisingly tight and it is because of this tightness that it may be incorporated into the software control of a bioreactor, such as a WAVE or Xuri™ bioreactor. This means that cell number can be predicted and perfusion rates can be changed without having to take a sample from the cellbags.

Figure 3:
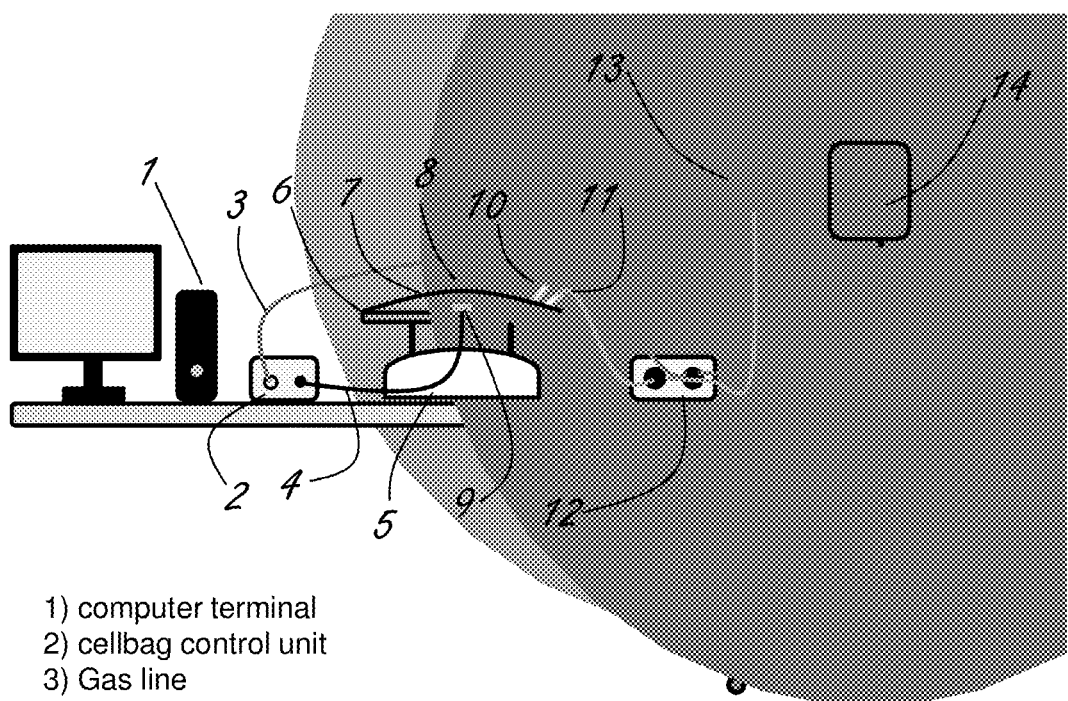
FIG. 3 is a schematic view of a bioreactor system according to the invention and shows the main features of the invention.

A preferred example of the bioreactor system of the invention is shown in FIG. 3 wherein (1) is a computer terminal, (2) a cellbag bioreactor control unit, (3) a gas outlet line, (4) a DO optical cable, (5) a Xuri™ Cell Expansion System, (6) a rocking platform, (7) a cellbag bioreactor, (8) a gas inlet port, (9) an optical probe for measuring DO, (10) a media waste line, (11) a media feed line, (12) and pump unit, (13) a media feed reservoir and (14) a media waste reservoir. The pump unit, the Xuri™ Cell Expansion System and cellbag Bioreactor Control Unit are connected to the computer terminal. Software in the computer terminal controls the rate that the pump unit operates which controls the rate of media exchange.

Figure 4:
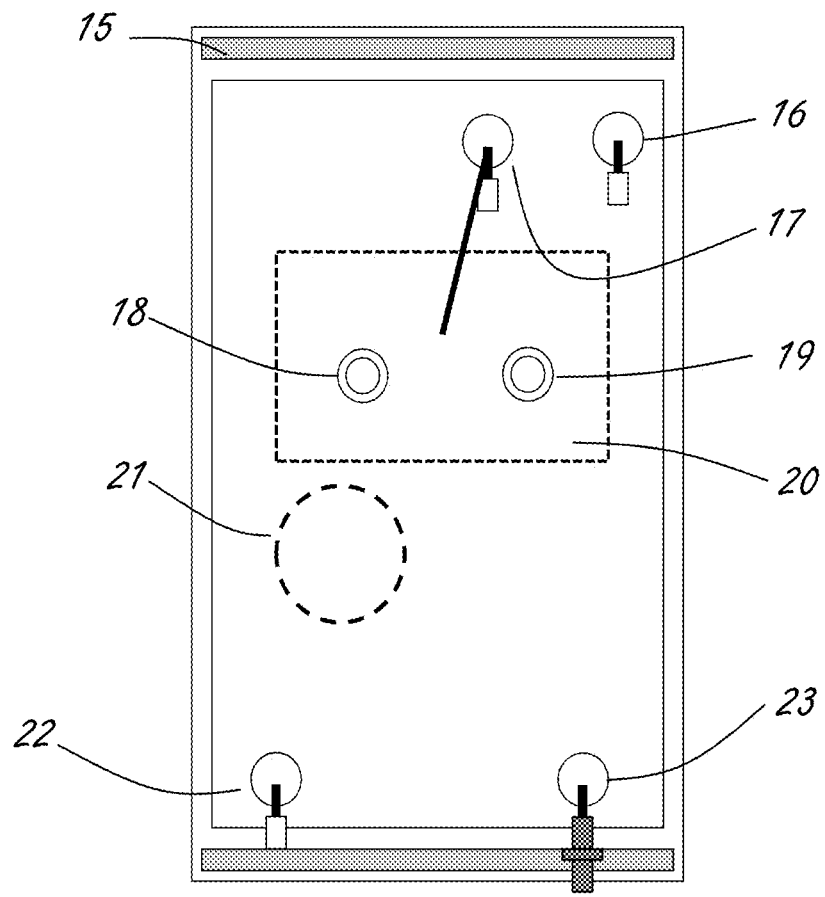
FIG. 4 is a schematic view of a cellbag used in the bioreactor system of FIG. 3.

FIG. 4 shows a cellbag for use in the bioreactor system of FIG. 3 comprising of (15) the fastening rods for attachment to the rocking platform, (16) a feed line, (17) a waste line, (18) a gas exhaust tube, (19) a gas inlet tube, (20) a perfusion filter, (21) an optical probe to measure dissolved oxygen, (22) a harvest port and (23) a sampling port. The perfusion filter is internal to the cellbag. The DO probe is embedded in the bottom of the cellbag and is in direct contact with the culture environment.

EXAMPLE 1

Defining the Relationship Between Dissolved Oxygen Levels and Cell Concentration Method: Peripheral Blood Mononuclear cells were cultured in static culture with anti-CD3/28 activation beads and 20 ng/ml of IL-2 for 5 days. During static culture the cell concentration was maintained at $5 \times 10E05$/ml though the addition of media. At day 5 of culture the cells were transferred to a 2 L cellbag for culture on the Xuri W25 bioreactor for a further 5-9 days. Cells were maintained at $5 \times 10E05$/ml through the addition of media until the final volume of 1 L had been reached, after which the cell concentration was allowed to increase as the cells continued to proliferate. The rocking platform was set at an angle of 6° and a rock rate of 15 rpm and kept constant throughout the course of the culture. Media perfusion was enabled once the cell concentration had reached $2 \times 10E06$/ml. The cellbags contained optical sensors for dissolved oxygen (DO) and measurement of DO levels were recorded every 24 hrs simultaneously with a cell count being taken. These data were compiled from 7 independent experiments, each using a different donor.

Figure 1:
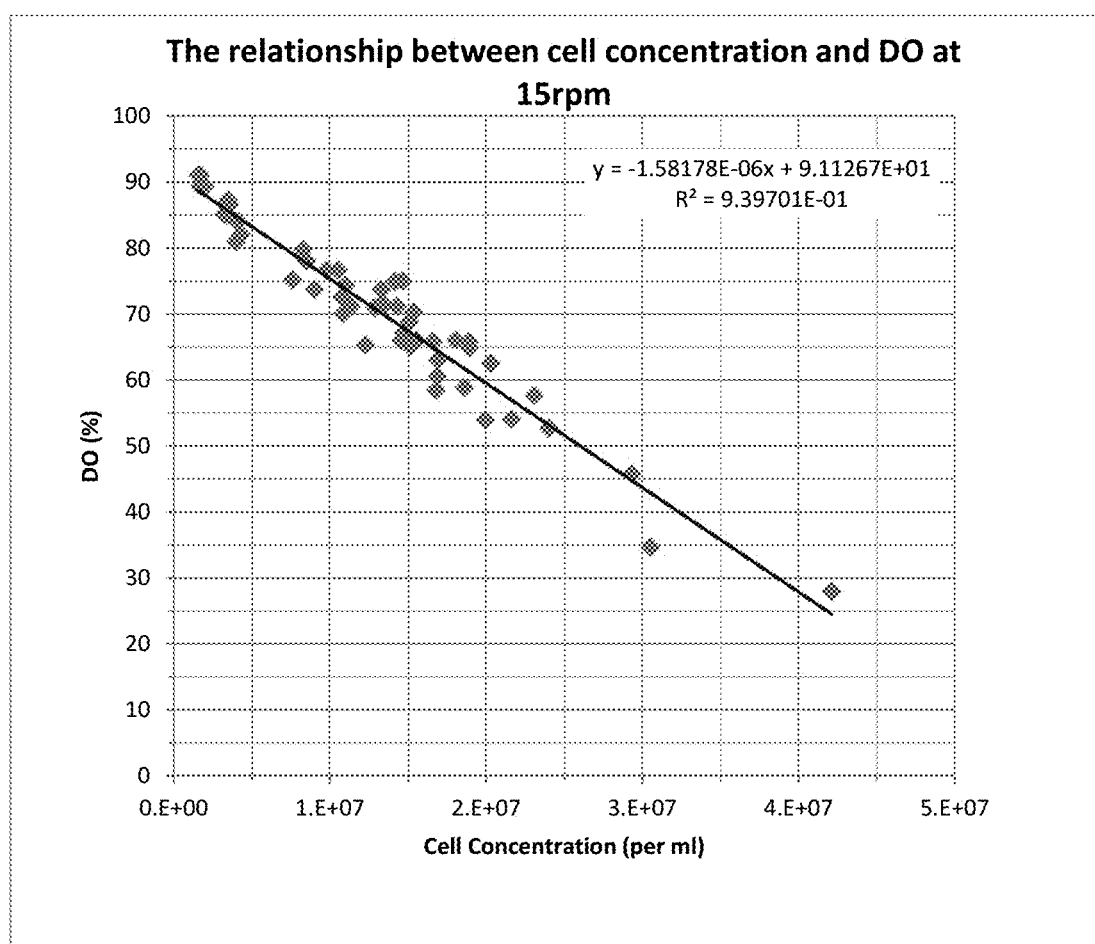
FIG. 1 shows data of an inverse linear relationship between dissolved oxygen (DO) concentration and concentration of primary human T cells in a 1 L culture on a Xuri™ bioreactor set at an angle of 6° and a rocking rate of 15 rpm of the bioreactor platform.

A plot of DO verses cell concentration was drawn and a linear trendline determined (FIG. 1). The formula of the trendline in this example was $$DO = -1.58E\text{-}06 * \text{Cell density} + 90.01$$

Using this formula the cell density of a given culture could be predicted from the DO readings at any point during the culture period provided the rocking rate was maintained at 15 rpm and the rocking angle was maintained at 6°.

Figure 2:
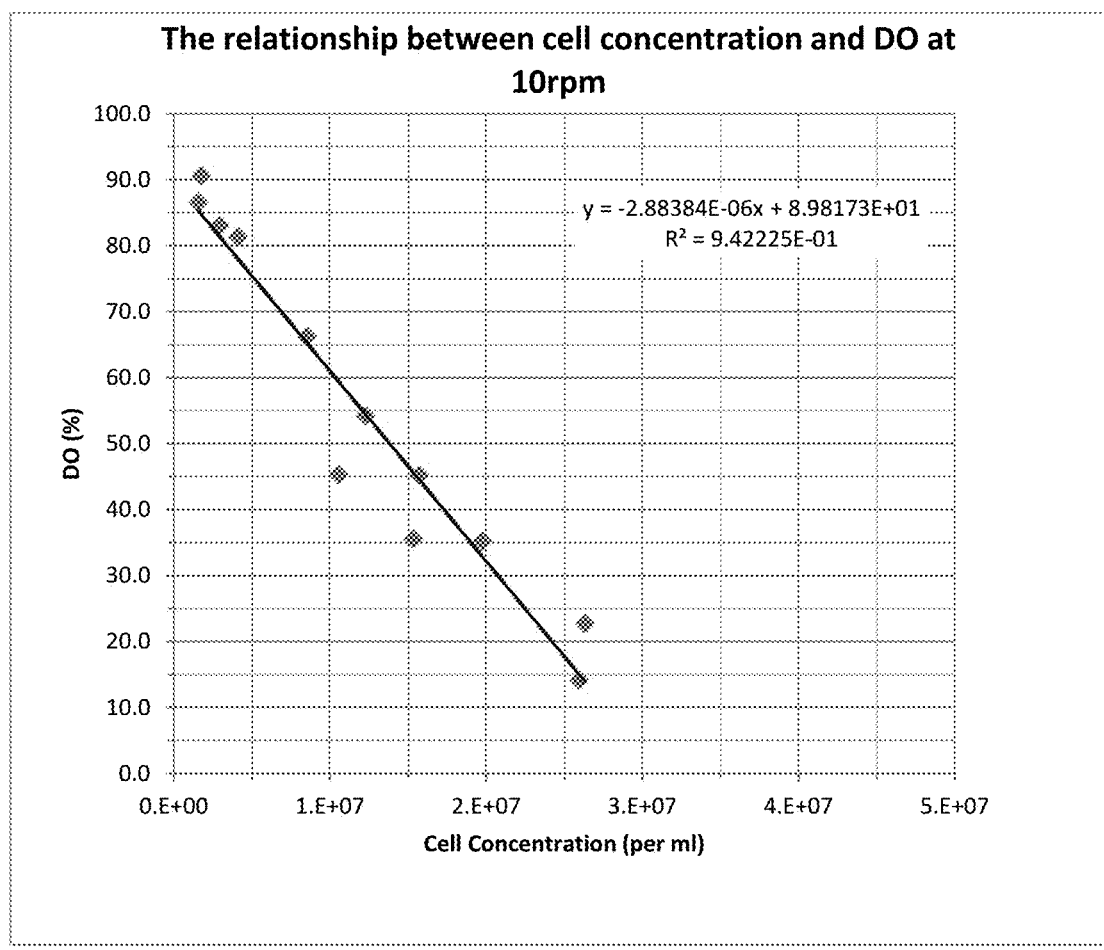
FIG. 2 shows the relationship between DO and cell concentration when the Xuri™ bioreactor is set at a rock rate of 10 rpm and at a 6° angle.

The same data was generated for cultures where the rocking platform was set at 10 rpm and 6° (FIG. 2). The data was compiled from two separate experiments using 2 donors. A plot of DO versus cell concentration was drawn and a trendline with formula generated. The formula of the trendline in this example was $$DO = -2.88E\text{-}06 * \text{Cell density} + 89.81$$

These data show that the slope of the line is dependent on the rocking rate of the bioreactor. Therefor to use these formulas to predict cell density the rocking conditions must be kept constant throughout the culture period.

EXAMPLE 2

Predicting Perfusion Rates Based on Dissolved Oxygen Readings

The ability to use DO to predict cell density can be further exploited to include an automated method of setting perfusion rates in T cell cultures. Perfusion rates are dictated by cell density, as the higher the number of cells, the higher the metabolic load and the greater the rate of media exchange that is required.

The standard perfusion rates used in the above experiments were as follows

| Cell concentration | Perfusion rate |
|---|---|
| $2 \times 10^6$/ml | 500 ml/day |
| $10 \times 10^6$/ml | 750 ml/day |
| $15 \times 10^6$/ml | 1000 ml/day |

Based on the trendlines of DO vs cell concentrations, the perfusion rates can be set using DO readings instead of cell concentration

| DO reading at 15 rpm | Do reading at 10 rpm | Perfusion rate |
|---|---|---|
| >88 | >84 | none |
| 75-88 | 61-84 | 500 ml/day |
| 67-75 | 47-61 | 750 ml/day |
| <67 | <47 | 1000 ml/day |

An automated set-up can be configured (FIG. 3) whereby the DO readings, which are collected continuously throughout the culture via the DO optical sensor embedded in the Cellbag bioreactor (FIG. 4) are recorded by the software and the software then adjusts the pump rates that control the amount of media to be perfused in the Cellbag bioreactor. This would eliminate the need for manual changing of the perfusion rates by the operator during the culture period. At the beginning of the bioreactor culture the operator would be required to instruct the software which perfusion rate to use based on the DO readings, as exemplified in the above table, but thereafter no further input from the operator would be required.

The invention claimed is:

1. A method for regulating perfusion rate in a suspension culture of cells comprising primary mononuclear cells in a non-static bioreactor, comprising:
    keeping the non-static bioreactor at a constant rocking rate of 1-25 rpm;
    registering the dissolved oxygen concentration in the bioreactor;
    determining the cell number of said primary mononuclear cells by a pre-determined correlation of the registered dissolved oxygen concentration with the cell number; and
    automatically controlling the perfusion rate in response to the registered dissolved oxygen concentration,
    wherein the pre-determined correlation is an inverse linear relationship, and
    wherein no sampling of the contents of the bioreactor is performed to determine cell number.

2. The method according to claim 1, wherein the dissolved oxygen concentration is measured by a sensor integrated in the bioreactor.

3. The method according to claim 1, wherein the bioreactor is a flexible cell bag.

4. The method according to claim 1, wherein the cells are T-cells.

5. The method according to claim 1, wherein the rocking rate is 10-15 rpm and the bioreactor is a flexible cell bag.

6. The method according to claim 1, wherein the rocking rate of the bioreactor is 10-15 rpm.

7. The method according to claim 2, wherein the sensor is an optical sensor.

8. The method according to claim 1, wherein the dissolved oxygen uptake is greater than 10%.

9. The method according to claim 1, wherein the pre-determined correlation of the registered dissolved oxygen concentration (DO) with the cell number is defined by linear relationships:

$$DO = -1.58E\text{-}06 * \text{cell density} + 90.01 \text{ at 15 rpm and } 6° \text{ angle; or}$$

$$DO = -2.88E\text{-}06 * \text{cell density} + 89.81 \text{ at 10 rpm and } 6° \text{ angle.}$$

10. The method according to claim 1, wherein controlling the perfusion rate in response to the registered dissolved oxygen concentration comprises adjusting pump rates without operator input.

11. The method according to claim 10, wherein the pump rates control an amount of media perfused in in the non-static bioreactor.

* * * * *